(12) United States Patent
Roe

(10) Patent No.: US 7,394,392 B1
(45) Date of Patent: *Jul. 1, 2008

(54) EXPERT SYSTEM SAFETY SCREENING OF EQUIPMENT OPERATORS

(76) Inventor: Kevin Roe, 4975 Moorpark Ave., San Jose, CA (US) 95129

(*) Notice: Subject to any disclaimer, the term of this patent is extended or adjusted under 35 U.S.C. 154(b) by 420 days.

This patent is subject to a terminal disclaimer.

(21) Appl. No.: 11/150,746

(22) Filed: Jun. 10, 2005

Related U.S. Application Data

(63) Continuation-in-part of application No. 11/143,830, filed on Jun. 2, 2005, now Pat. No. 7,227,472, and a continuation-in-part of application No. 11/145,702, filed on Jun. 6, 2005.

(51) Int. Cl.
*G08B 23/00* (2006.01)

(52) U.S. Cl. .............. 340/576; 340/500; 340/573.1; 180/272

(58) Field of Classification Search ............. 340/576, 340/500, 573.1, 632; 422/84; 73/23.3, 19.01; 180/272; 600/363, 532
See application file for complete search history.

(56) References Cited

U.S. PATENT DOCUMENTS

| | | | |
|---|---|---|---|
| 3,811,116 A | 5/1974 | Takeuchi et al. | |
| 3,823,382 A | 7/1974 | Gaddy | |
| 4,592,443 A | 6/1986 | Simon | |
| 4,613,845 A | 9/1986 | DuBois | |
| 4,738,333 A | 4/1988 | Collier et al. | |
| 4,996,161 A | 2/1991 | Conners et al. | |
| 5,344,324 A * | 9/1994 | O'Donnell et al. | 434/258 |
| 5,692,502 A * | 12/1997 | Alpert | 600/300 |
| 5,793,292 A | 8/1998 | Ivey, Jr. et al. | |
| 5,969,615 A | 10/1999 | Ivey, Jr. et al. | |
| 6,229,908 B1 * | 5/2001 | Edmonds et al. | 382/124 |
| 6,748,301 B1 | 6/2004 | Ryu | |
| 6,886,653 B1 | 5/2005 | Bellehumeur | |
| 2002/0084130 A1 | 7/2002 | Der Ghazarfan et al. | |

* cited by examiner

*Primary Examiner*—Anh V La
(74) *Attorney, Agent, or Firm*—Kevin Roe

(57) ABSTRACT

Methods and systems using one or more expert systems to screen equipment operators for impairments, such as intoxication, physical impairment, medical impairment, or emotional impairment, to selectively test the equipment operators and control the equipment (e.g., automobiles, trucks, industrial vehicles, public transportation vehicles, such as buses, subways, trains, planes, and ships, and dangerous machinery in general) if impairment of the equipment operator is determined. One embodiment is a method to screen an equipment operator for intoxication, using one or more expert systems. A second embodiment is a method to screen an equipment operator for impairment, such as intoxication, physical impairment, medical impairment, or emotional impairment, using one or more expert systems. A third embodiment is an equipment operator screening system to determine impairment, such as intoxication, physical impairment, medical impairment, or emotional impairment, using one or more expert systems.

18 Claims, 16 Drawing Sheets

EXPERT SYSTEM SAFETY SCREENING OF EQUIPMENT OPERATORS

CROSS-REFERENCE TO RELATED APPLICATIONS

This application is a continuation-in-part of a U.S. utility patent application, Ser. No. 11/143,830, filed by the same inventor on Jun. 2, 2005, entitled "Multistage Safety Screening of Equipment Operators," which issued as U.S. Pat. No. 7,227,472 on Jun. 5, 2007, and a U.S. utility patent application, Ser. No. 11/145,702, filed by the same inventor on Jun. 6, 2005, entitled "Integrated Safety Screening of Equipment Operators," which are hereby both incorporated by reference.

BACKGROUND OF THE INVENTION

1. Field of the Invention

This invention relates generally to controlling the operation of equipment by impaired operators, and more specifically to controlling the operation of equipment by operators who show intoxication or other impairment as determined by an expert system safety screening.

2. Description of the Prior Art

Intoxicated or otherwise impaired equipment operators (e.g., physically impaired, medically impaired, or emotionally impaired operators) of equipment (e.g., automobiles, trucks, industrial vehicles, public transportation vehicles, such as buses, subways, trains, planes, and ships, and dangerous machinery in general) needlessly continue to cause many thousands of horrible deaths and injuries each year around the world. The main focus of previous efforts has been alcoholic or drug intoxication of vehicle operators, since this continues to be the most prevalent type of dangerous equipment operator impairment. Though systems have been devised that disable a vehicle based on an operator's alcohol level, such systems have been too complex, and have not been employed as they are usually too expensive, too annoying for an operator to tolerate on a daily basis, and/or simply too easy for an operator to circumvent. Some systems have used coordination measurement that requires the user to push buttons in a random order within a given amount of time in order to allow the vehicle to be started. Other systems have used detectors for analyzing the breath of the vehicle operator in order for the operator to start a vehicle.

U.S. Pat. No. 6,886,653 issued to Bellehumeur, on May 3, 2005, discloses a system including a galvanic skin sensor that can provide trans-dermal monitoring of a person's skin for ascertaining whether or not the person has consumed alcohol and the person's skin temperature. The sensor is connected through an actuating switch control system that is mounted electrically, typically within the vehicle ignition system that can act as a cutoff switch based on the various inputs from the trans-dermal sensor. The nature of this system appears likely to limit its use, but the disclosures of this patent are hereby incorporated by reference.

U.S. Pat. No. 6,748,301 issued to Ryu, on Jun. 8, 2004, discloses an apparatus and method for prevention of driving of motor vehicle under the influence of alcohol and prevention of vehicle theft, in which a voice and a voice secret code of an authorized driver is stored by learning through a voice recognition apparatus and microphone mounted in the vehicle, and then the breath of an intended operator is detected when the driver says the secret code to check whether or not the operator is legally drunk, and also the intended operator's voice secret code is compared to the stored voice and voice secret code. The driver is allowed to start the vehicle only when the operator is not legally drunk and the voice secret code matches the stored voice secret code. The nature of this system appears likely to limit its use, but the disclosures of this patent are hereby incorporated by reference.

U.S. Pat. App. No. 20020084130 published by Der Ghazarian, et al., on Jul. 4, 2002, discloses a voice recognition breathalyzer comprising a microphone for transducing spoken expression into electronic signals and a breathalyzer sensor for transducing breath content into electronic signals. It includes an audio and breathalyzer sensor circuit for conditioning the electronic signals from the microphone and breathalyzer sensor; a memory storage for storing speech templates and toxic breath setting; a processor for processing the conditioned electronic signals and for simultaneously comparing the processed, conditioned electronic signals with the speech templates and the toxic breath setting threshold stored in the memory storage, generating a unique signal when the processed, conditioned electronic signals are substantially similar to one of the speech templates and below the toxic breath setting threshold. The nature of this system appears likely to limit its use, but the disclosures of this patent application are hereby incorporated by reference.

U.S. Pat. No. 5,969,615 issued to Ivey Jr., et al., on Oct. 19, 1999, discloses a system for monitoring and covering the use of a hand-operated machine by an impaired individual through detection of toxins in the individual. This system uses vapor from an individual's hands drawn through a sampling apparatus. The resultant signal is used to estimate the alcoholic content of the individual. The nature of this system appears likely to limit its use, but the disclosures of this patent are hereby incorporated by reference.

U.S. Pat. No. 5,793,292 issued to Ivey Jr., on Aug. 11, 1998, discloses a device to prevent hand operated machines from being operated by an impaired individual by measuring toxins in the person using sensors that interact with the vehicle. The nature of this system appears likely to limit its use, but the disclosures of this patent are hereby incorporated by reference.

U.S. Pat. No. 4,996,161 issued to Conners, et al., on Feb. 26, 1991, discloses a breath alcohol testing system that may be used in conjunction with a vehicle. Although the breathanalyzer may be highly accurate, its interaction with a vehicle that requires a person to breathe into a facemask is likely to annoy the operator. The nature of this system appears likely to limit its use, but the disclosures of this patent are hereby incorporated by reference.

U.S. Pat. No. 4,738,333 issued to Collier, et al., on Apr. 19, 1988, discloses a sobriety interlock system that prevents a vehicle or other equipment from being started unless the identity of a designated operator is confirmed by the system and the operator passes a breath sobriety test. The designated operator is trained to perform a physical act, the successful completion of which can be determined by the system and which requires at least a predetermined number, N, of attempts to learn. A necessary precondition for starting the vehicle is satisfied when the system determines that the identity-confirming act has been performed in fewer than N attempts. The nature of this system appears likely to limit its use, but the disclosures of this patent are hereby incorporated by reference.

U.S. Pat. No. 4,613,845 issued to DuBois, on Sep. 23, 1986, discloses an apparatus for preventing operation of machinery by an intoxicated operator, using an alcohol sensor located near the control panel on a portion of the steering wheel. The nature of this system appears likely to limit its use, but the disclosures of this patent are hereby incorporated by reference.

U.S. Pat. No. 4,592,443 issued to Simon, on Jun. 3, 1986, discloses a sobriety interlock that includes an apparatus for detecting alcohol on the breath that is connected to the ignition system of a vehicle. The nature of this system appears likely to limit its use, but the disclosures of this patent are hereby incorporated by reference.

U.S. Pat. No. 3,823,382 issued to Gaddy, on Jul. 9, 1974, discloses a system for inhibiting motor vehicle operation by intoxicated drivers. This device uses a breath-analyzer that measures the alcohol level using a chemical reaction in order to prevent the car from starting. The nature of this system appears likely to limit its use, but the disclosures of this patent are hereby incorporated by reference.

U.S. Pat. No. 3,811,116 issued to Takeuchi, et al., on May 14, 1974, discloses a device for detecting mental impairment in a driver that includes a degree of fatigue or drunkenness, judging the mental ability of the operator for operating a vehicle. The nature of this system appears likely to limit its use, but the disclosures of this patent are hereby incorporated by reference.

While many of the systems in the prior art cleverly and impressively attempt to solve the problem of preventing a person who is intoxicated from operating a vehicle, the systems typically can still be circumvented by accident or by intent. Furthermore, these systems usually cannot detect the physically impaired, medically impaired, or emotionally impaired operators if they are otherwise sober. And due to their time-consuming or intrusive nature, they are usually likely to annoy an operator to such an extent as to motivate the operator to do whatever is necessary to intentionally circumvent the system, defeating the entire purpose of the system. Furthermore, any one prior art system alone can experience a likelihood of incorrectly detecting operator intoxication or impairment when the operator is not intoxicated or impaired (i.e., a false positive), or incorrectly missing operator intoxication or impairment when the operator is truly intoxicated or otherwise truly impaired (i.e., a false negative).

What is needed is a system that overcomes these problems with a screening approach to minimize the annoyance to an equipment operator and increase the probability of correctly controlling the operation of equipment by a truly intoxicated or otherwise truly impaired equipment operator.

SUMMARY OF THE INVENTION

The present invention overcomes the problems of the prior art by using an expert system safety screening approach to minimize the annoyance to an equipment operator and increase the probability of safely controlling the operation of equipment (e.g., automobiles, trucks, industrial vehicles, public transportation vehicles, such as buses, subways, trains, planes, and ships, and dangerous machinery in general) by a truly intoxicated or otherwise truly impaired equipment operator. Embodiments of the invention can be implemented in numerous ways. Three aspects of the invention are described below.

A first aspect of the invention is directed to a method to screen an equipment operator for intoxication. The method includes screening an equipment operator by an expert system to detect potential intoxication; selectively testing the equipment operator when the screening indicates potential intoxication of the equipment operator; and controlling the operation of the equipment if the selective testing of the equipment operator indicates intoxication of the equipment operator.

A second aspect of the invention is directed to a method to screen an equipment operator for impairment. The method includes screening an equipment operator by an expert system to detect potential impairment of the equipment operator; selectively testing the equipment operator when the screening of the equipment operator detects potential impairment of the equipment operator; and controlling the operation of the equipment if the selective testing of the equipment operator indicates the impairment of the equipment operator.

A third aspect of the invention is directed to a system to screen an equipment operator. The system includes a screening module to detect potential impairment of an equipment operator and selectively test the equipment operator when potential impairment of the equipment operator is detected, wherein the screening module includes one or more expert system modules in screening the equipment operator, and a control module to control the operation of the equipment if the selective testing of the equipment operator by the screening module indicates the impairment of the equipment operator.

DETAILED DESCRIPTION OF THE PREFERRED EMBODIMENT

Figure 1:
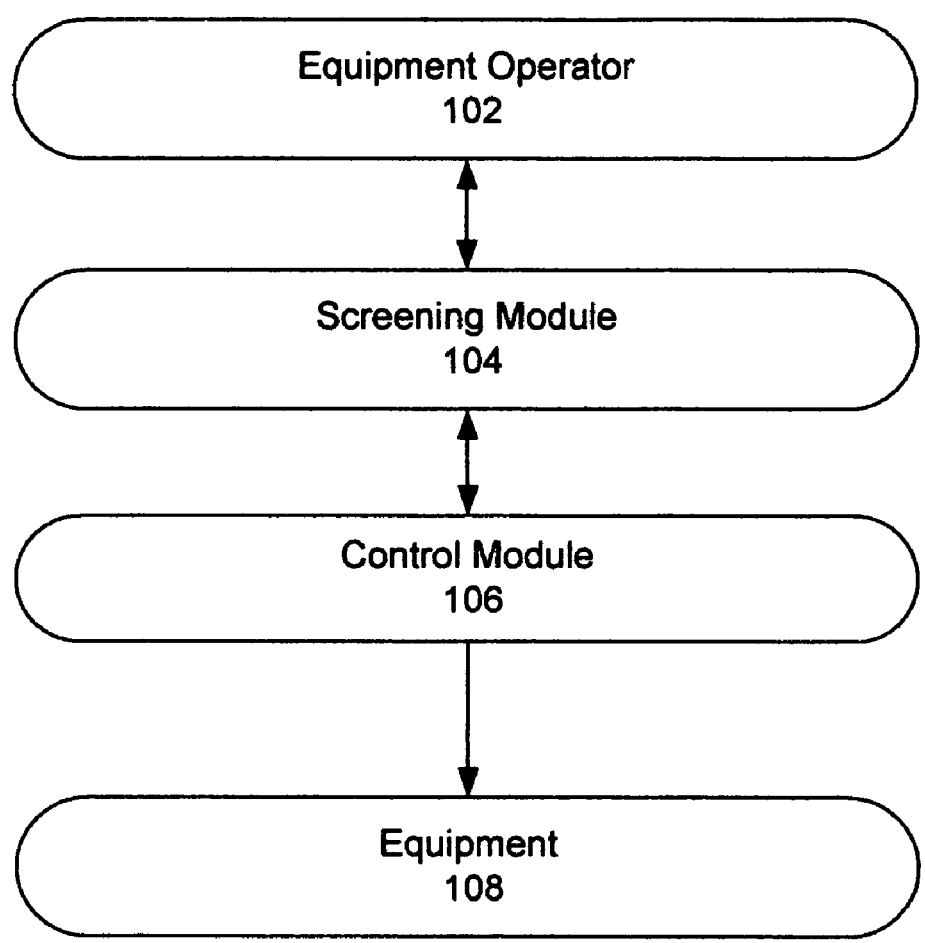
FIG. 1 illustrates a module diagram of a system to screen an equipment operator, in accordance with one embodiment of the invention.

The primary goal of any embodiment of the present invention is to control the operation of equipment by an equipment operator when there is a very high probability that there is equipment operator impairment, such as intoxication (e.g., alcohol intoxication, chemical intoxication, or equivalent conditions), physical impairment (e.g., sudden injury from accident or violence against the equipment operator, blindness, lack of air, a poisonous or disabling gas or dust, or equivalent conditions), medical impairment (e.g., stroke, heart attack, diabetic coma, exhaustion, infectious disease, or equivalent conditions), or emotional impairment (e.g., grief, anger, psychosis, anxiety, euphoria, or equivalent conditions). Due to the great inconvenience, any practical embodiment must have a very low probability of false positives (i.e., controlling/preventing the operation of equipment by an equipment operator because of an incorrect determination of impairment, such as intoxication, physical impairment, medical impairment, or emotional impairment). Furthermore, due to the great danger, any practical embodiment must also have a very low probability of false negatives (i.e., allowing an impaired equipment operator to operate the equipment because of an incorrect determination of non-impairment). An expert system screening of the equipment operator for impairment will significantly increase the accuracy of the screening and decrease both the probability of a false positive and a false negative.

Various embodiments of the invention are possible, but one embodiment method includes measuring at least one type of chemical (e.g., ethanol, carbon monoxide, carbon dioxide, hydrocarbon vapors, nitrous oxide levels, or any other regulated mind-impairing chemical, such as cannabis, amphetamines, cocaine, glue vapors, and equivalents) in the air in proximity to an equipment operator (e.g., within an operator compartment), wherein the type of chemical is associated with impairment. Selective testing of the equipment operator can proceed when at least one type of chemical is detected at a sufficient level to indicate impairment of the equipment operator.

One embodiment of the invention also includes measuring at least one characteristic of the equipment operator that is associated with impairment, such as intoxication, physical impairment, medical impairment, or emotional impairment. Depending of the results of the measurement of at least one characteristic of the equipment operator, selective testing of the equipment operator can further determine whether the equipment operator is truly impaired and control operation of the equipment. The selective testing of the equipment operator can either require the active participation and knowledge of the equipment operator. The selective testing of the equipment operator can also increase in extent if the initial testing indicates possible impairment, such as intoxication, physical impairment, medical impairment, or emotional impairment.

Embodiments of the invention can be constructed from various combinations of screening modules to selectively measure various characteristics of an equipment operator. The screening modules can measure a characteristic of the equipment operator, such as a chemical in proximity to the equipment operator, electrical resistance of a portion of skin of the equipment operator, breathing rate of the equipment operator, blood pressure of the equipment operator, blood pulse rate of the equipment operator, blood oxygen level of the equipment operator, electrical conductivity of a portion of skin of the equipment operator, temperature of a portion of skin of the equipment operator, one or more optical characteristics of at least one eye of the equipment operator, optical response to at least one stimulus of at least one eye of the equipment operator, at least one speech characteristic of the equipment operator, comparison of at least one speech characteristic of the equipment operator to a sample speech characteristic of the equipment operator, a speed of dexterity of the equipment operator in performing at least one task, and a consistency of dexterity of the equipment operator in performing at least one task.

Embodiments of the invention can be implemented by utilizing combinations of one or more modules (e.g., using all of a module, or using a portion of a module) already existing in the equipment as standard features. For example, in a typical vehicle there is an operations module (e.g., an equipment operations module allowing the equipment operator to determine one or more functions of equipment, such as speed of operation and direction of movement), an audio module (e.g., a sound entertainment module, or a communication module), a navigation module (e.g., a map display module), an anti-theft module (e.g., a motion detector module), and a climate control module (e.g., an air-conditioning module). Many of these modules have become very sophisticated in their operator interfaces and in their convenience to the equipment operator. These existing modules also can provide useful information on past and/or current operator actions to assist in the process of determining whether the equipment operator is truly impaired or not impaired.

There are at least ten major advantages to using expert system screening in conjunction with already existing modules in equipment to detect an impairment in an equipment operator. The advantages are (1) the equipment operator is much less likely to deactivate or damage existing modules because of their fundamental convenience and utility to the operator, (2) the equipment operator is already familiar and comfortable interacting with the existing modules and less likely to avoid them, (3) the equipment operator is already knowledgeable in interacting with existing modules and therefore does not need extensive additional training to interact with an entirely new module, (4) the transducers and/or operator displays are more trusted by the operator even while being used for screening purposes, (5) some existing modules already have useful information about the history of the equipment operator that can improve the accuracy of the determination of impairment, (6) speech synthesis and/or speech recognition systems in the existing modules can be utilized in the screening of the equipment operator to determine impairment, (7) use of existing modules greatly reduces the screening cost, (8) overall equipment reliability is increased, since the use of existing modules reduces the total complexity and probability of failure of the components needed for a safety screening, (9) less space is needed in the equipment operator compartment, and (10) less electrical power is needed to conduct the screening.

Embodiments of the invention can be constructed using one or more data processing systems already existing in the equipment modules listed above, in a time-sharing allocation of their available processors and memory. Such existing equipment modules frequently have some unused memory and unused processor time available after performing their existing module functions. Alternatively, one or more additional data processing systems (e.g., based on any commercially available microprocessor of any word bit width and clock speed, a control Read-Only-Memory, or a data processing equivalent) can be dedicated to combining the information gathered from one or more modules listed above, or disclosed by one or more of the prior art patents incorporated by reference.

One embodiment of the invention uses one or more expert system modules to screen and/or selectively test an equipment operator to determine whether or not there is a true impairment. Such expert system modules can be executed in one or more dedicated data processing systems, and/or executed in a time-sharing allocation on one or more of the processors already existing in one or more of the modules listed above (e.g., operations module, audio module, navigation module, an anti-theft module, a climate control module, or an equivalent module normally associated with the equipment).

One embodiment of the invention also utilizes one or more expert system modules to screen and/or selectively test an equipment operator by one or more interactions and evaluate the responses of the equipment operator to the interactions to determine whether or not there is a true impairment of the equipment operator. These interactions can include sound exchanges, visual exchanges, and/or physical exchanges. A sound exchange includes one or more types of speech, hearing, and/or sound games to evaluate the equipment operator. A visual exchange includes one or more types of visual games to evaluate the equipment operator using one or more operator displays. A physical exchange includes one or more types of dexterity games to evaluate the equipment operator. One or more of these evaluations can be used to adapt or perform the screening and/or selective testing of the equipment operator to more quickly and more accurately determine whether there is a true impairment of the equipment operator.

One embodiment of the invention also includes a screening module that permits screening and/or selective testing of an equipment operator upon activation by the equipment operator and/or one or more people in proximity to the equipment operator. In one embodiment, the equipment operator and/or one or more people in proximity to the equipment operator can verbally or physically activate a screening of said equipment operator for intoxication or another impairment by one or more expert systems.

One embodiment of the invention also includes selective testing that selectively changes according to one or more other factors, such as air temperature, oxygen levels, carbon dioxide levels, carbon monoxide levels, nitrous oxide levels, hydrocarbon vapor levels, the presence of any gas associated with impairment, air humidity, air pressure, time of day, time duration of vehicle parking, voice loudness levels in proximity to the equipment, history of operation of the equipment by the equipment operator, initial beginning of operation of the equipment by the equipment operator, and ongoing operation of the equipment by the equipment operator. In other words, one embodiment of the invention can screen the operator for impairment, such as intoxication, physical impairment, medical impairment, or emotional impairment acquired during the operation of the equipment, not just impairments already existing at the initial beginning of operation of the equipment. Some operators may initially be unimpaired when beginning equipment operation, and then become impaired during the operation due to the ingestion of impairing substances, or occurrence of other events, such as physical impairment, medical impairment, or emotional impairment.

Controlling the operation of equipment by an impaired equipment operator can include many possible types of control responses. Controlling the operation of the equipment can include one or more of the following control responses: disabling the equipment, disabling the equipment after a time delay, temporarily disabling the equipment for a pre-selected time duration, shutting off power to the equipment, limiting the operation of the equipment to a lower speed of operation, limiting the operation of the equipment to allow only the return the equipment to a pre-selected state or a pre-selected location, autonomously moving said equipment to another location, denying entry to the equipment, activating an alarm, sending a warning message to another entity for assistance, issuing a warning message to the impaired equipment operator, and/or requesting another equipment operator replace the impaired equipment operator and then restricting equipment operation if the request is not obeyed within a pre-selected time.

FIG. 1 illustrates a module diagram of a system to screen an equipment operator, in accordance with one embodiment of the invention. The screening module 104 screens equipment operator 102 to determine at least one type of potential impairment. In one embodiment, the screening module 104 includes one or more test systems disclosed in the prior art (computerized or non-computerized) that are available to screen, measure, or test humans or environments for unusual phenomena. In an alternative embodiment, the screening module 104 includes part or all of one or more of the intoxication detection systems taught in the prior art patents that have been previously listed and incorporated by reference. The screening module 104 determines whether the equipment operator 102 is impaired and whether to activate the control module 106. Control module 106 controls the equipment 108, using one or more of the control responses already listed above. For example, in one embodiment the control module 106 restricts operation of equipment 108 without delay, but in another embodiment the control module 106 restricts the equipment 108 after a message is provided to the equipment operator 102 requesting another equipment operator, restricting operation after such a request is not obeyed with a pre-selected time.

Figure 2:
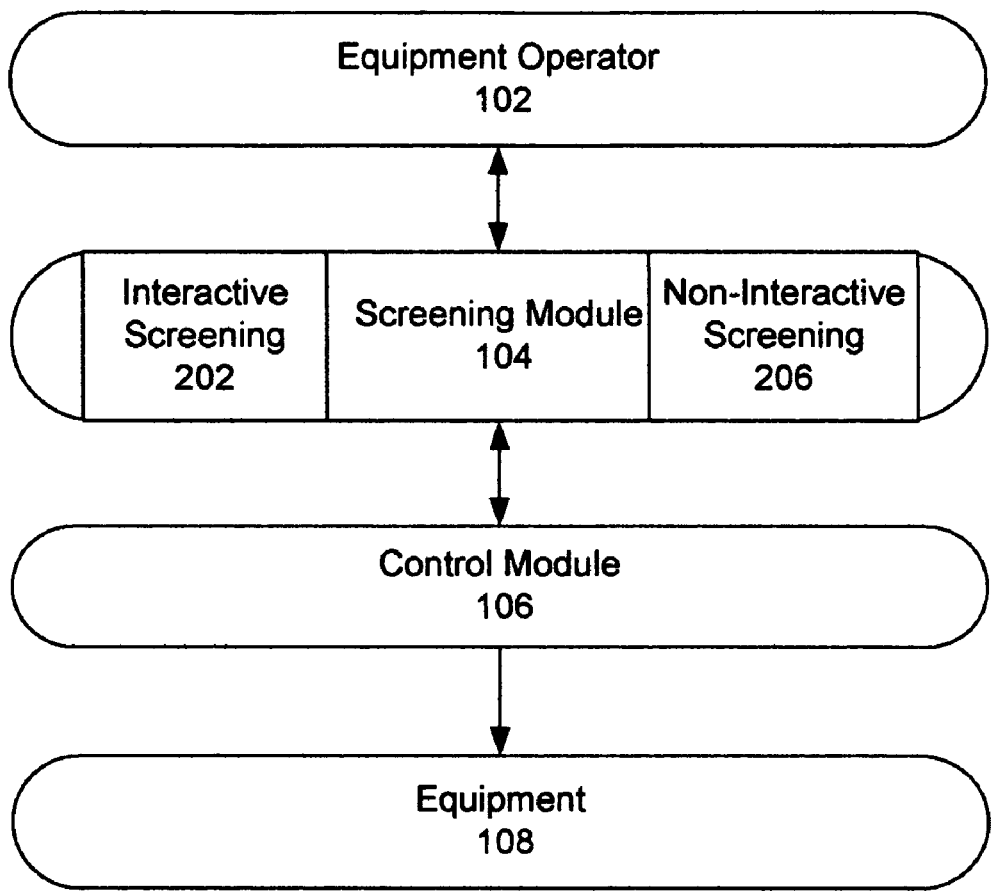
FIG. 2 illustrates a module diagram of a system to screen an equipment operator, in accordance with another embodiment of the invention.

FIG. 2 illustrates a module diagram of a system to screen an equipment operator, in accordance with one embodiment of the invention. The screening module 104 screens equipment operator 102 for one or more impairments, such as intoxication, physical impairment, medical impairment, or emotional impairment. The screening module 104 determines whether the equipment operator 102 is impaired and whether to activate the control module 106. Control module 106 controls the equipment 108, using one or more of the control responses listed above. In this embodiment of the invention, screening module 104 includes both interactive screening module 202 (which will screen the equipment operator 102 with the conscious interaction and awareness of the equipment operator 102) and non-interactive screening module 206 (which will screen the equipment operator 102 without the conscious interaction and awareness of the equipment operator 102).

Non-interactive screening module 206 can measure a characteristic of the equipment operator, such as a chemical in proximity to the equipment operator, electrical resistance of a portion of skin of the equipment operator, breathing rate of the equipment operator, blood pressure of the equipment operator, blood pulse rate of the equipment operator, blood oxygen level of the equipment operator, electrical conductivity of a portion of skin of the equipment operator, temperature of a portion of skin of the equipment operator, one or more optical characteristics of at least one eye of the equipment operator, optical response to at least one stimulus of at least one eye of the equipment operator, at least one speech characteristic of the equipment operator, comparison of at least one speech characteristic of the equipment operator to a sample speech characteristic of the equipment operator, a speed of dexterity of the equipment operator in performing at least one task, and a consistency of dexterity of the equipment operator in performing at least one task. Interactive screening module 202 can incorporate one or more features of the non-interactive screening module 206 and also ask the equipment operator to perform some task, such as speaking, interpreting a visual pattern, or physically moving some body part (e.g., hands or fingers).

One or both of the interactive screening module 202 and non-interactive screening module 206 can also access other relevant data to consider with the screening results in determining whether there is a true impairment of the equipment operator. Other factors data can include one or more factors, such as air temperature, oxygen levels, carbon dioxide levels, carbon monoxide levels, nitrous oxide levels, hydrocarbon vapor levels, the presence of any gas associated with impairment, air humidity, air pressure, time of day, time duration of vehicle parking, voice loudness levels in proximity to the equipment, history of operation of the equipment by the equipment operator, initial beginning of operation of the equipment by the equipment operator, and ongoing operation of the equipment by the equipment operator.

Figure 3:
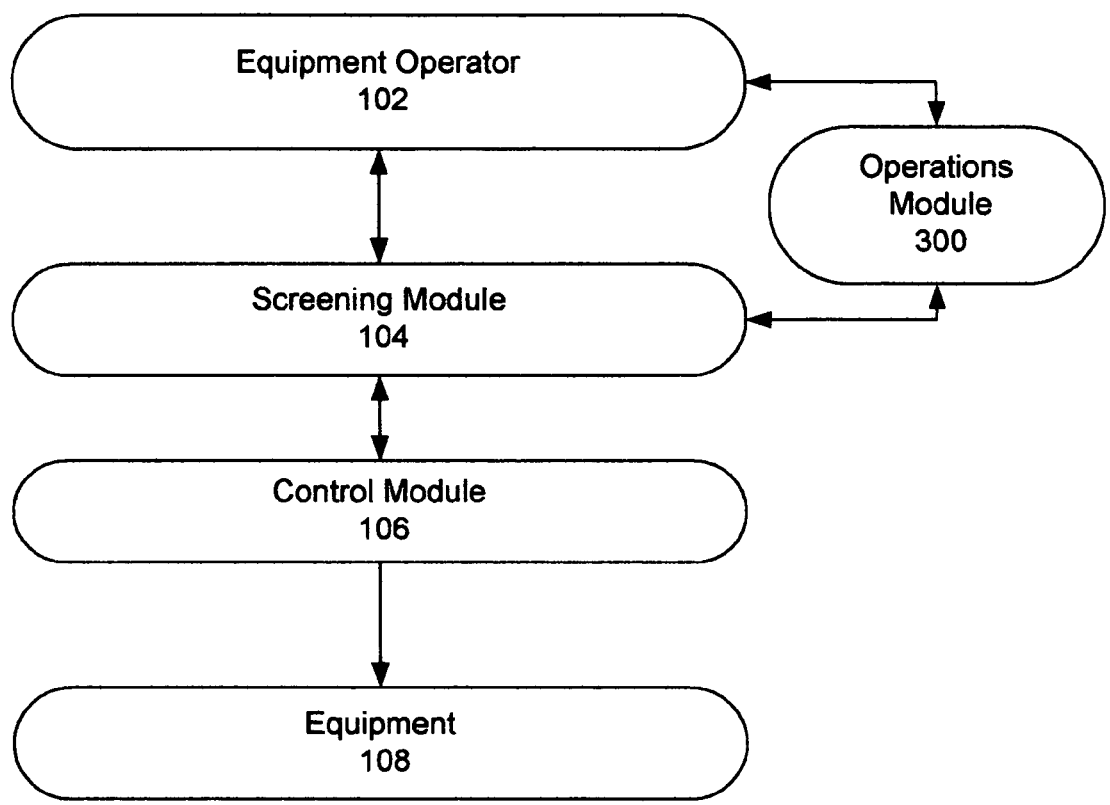
FIG. 3 illustrate a module diagram of a system to screen an equipment operator by utilizing an operations module of the equipment, in accordance with another embodiment of the invention.

FIG. 3 illustrates a module diagram of a system to screen an equipment operator by utilizing an operations module of the equipment, in accordance with another embodiment of the invention shown in FIG. 1. The screening module 104 screens the equipment operator 102 for one or more impairments. The screening module 104 utilizes information from operations module 300 to determine whether the equipment operator 102 is impaired and whether to active the control module 106. Control module 106 controls the equipment 108, using one or more of the control responses listed above. The operations module 300 in some embodiments includes speech synthesis and/or speech recognition subsystems that can be integrated with little additional cost with the screening module 104 to expand the extent of the screening to include speech communication and speech analysis of the equipment operator 102. The operations module 300 in one embodiment also provides historical information useful for more accurately screening the equipment operator 102 for impairments.

Figure 4:
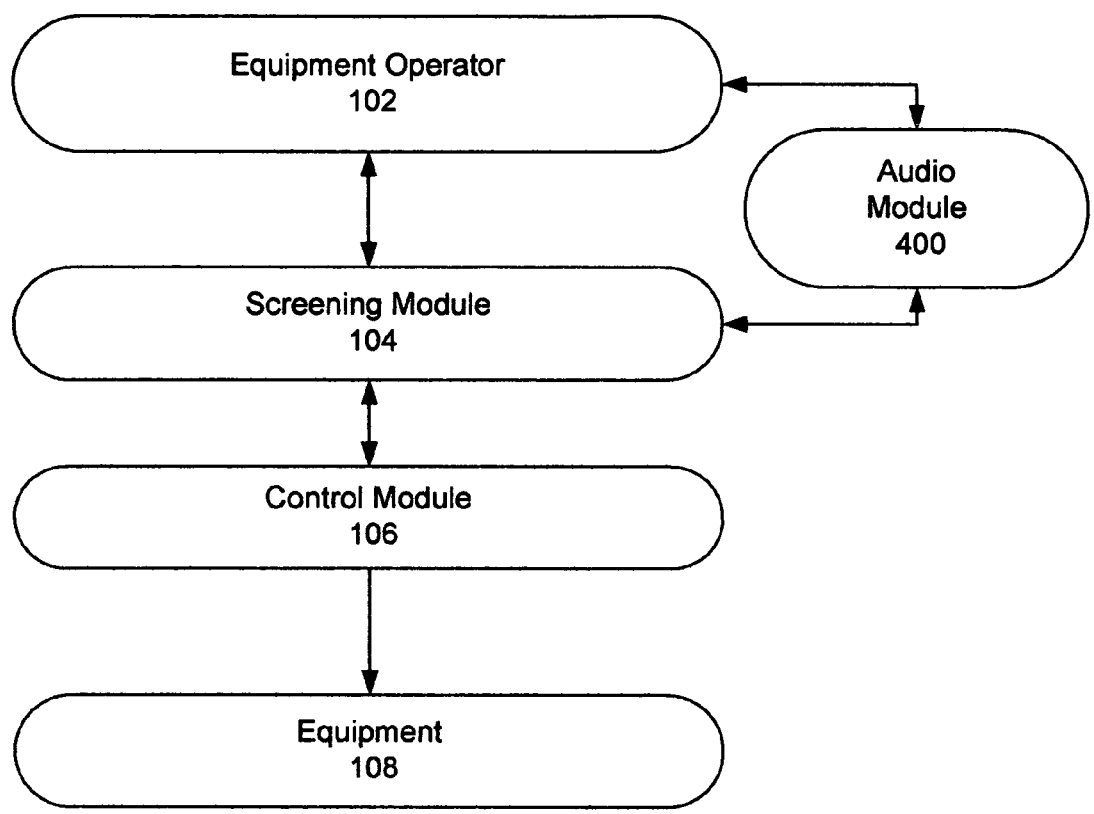
FIG. 4 illustrates a module diagram of a system to screen an equipment operator by utilizing an audio module of the equipment, in accordance with another embodiment of the invention.

FIG. 4 illustrates a module diagram of a system to screen an equipment operator by utilizing an audio module of the equipment, in accordance with another embodiment of the invention shown in FIG. 1. The screening module 104 screens the equipment operator 102 for one or more impairments. The screening module 104 utilizes information from audio module 400 to determine whether the equipment operator 102 is impaired and whether to activate the control module 106. Control module 106 controls the equipment 108, using one or more of the control responses listed above. The audio module 400 in some embodiments includes speech synthesis and/or speech recognition subsystems that can be integrated with little additional cost with the screening module 104 to expand the extent of the screenings to include speech communication and speech analysis of the equipment operator 102. The audio module 400 in one embodiment also provides historical information useful for more accurately screening the equipment operator 102 for impairments.

Figure 5:
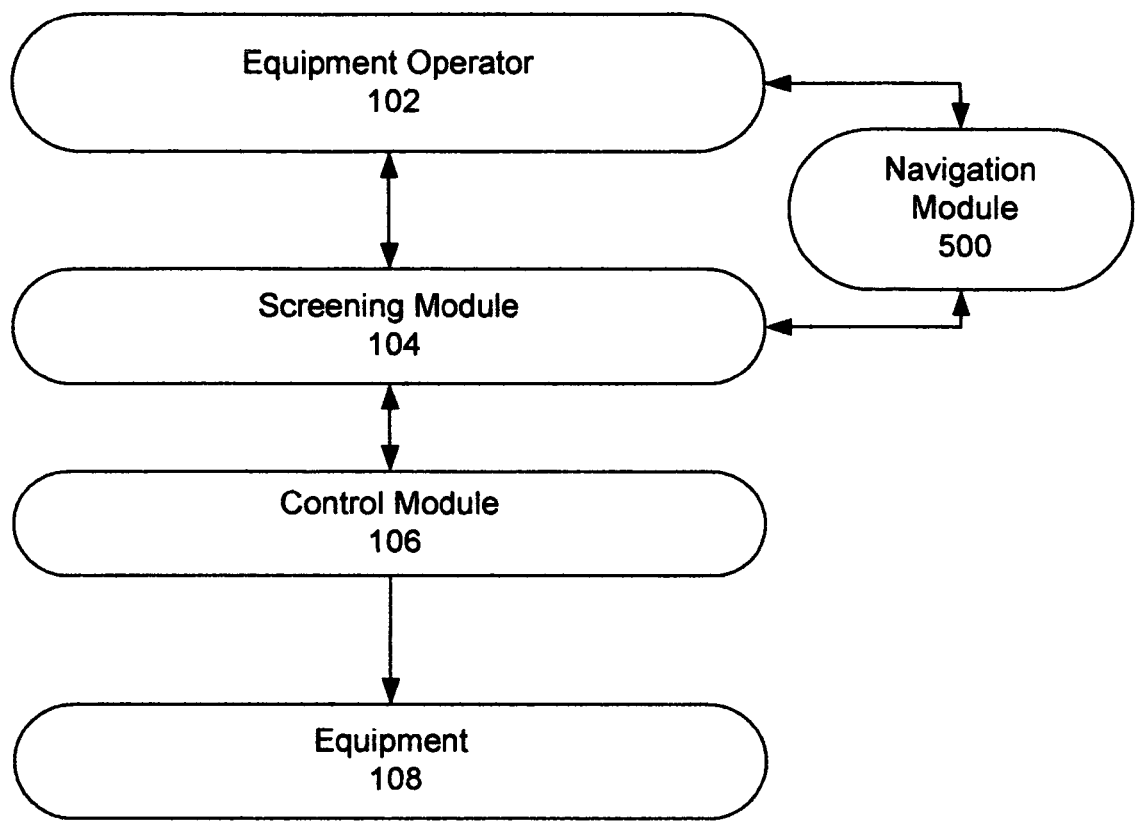
FIG. 5 illustrates a module diagram of a system to screen an equipment operator by utilizing a navigation module of the equipment, in accordance with another embodiment of the invention.

FIG. 5 illustrates a module diagram of a system to screen an equipment operator by utilizing a navigation module of the equipment, in accordance with another embodiment of the invention shown in FIG. 1. The screening module 104 screens the equipment operator 102 for one or more impairments. The screening module 104 utilizes information from the navigation module 500 to determine whether the equipment operator 102 is impaired and whether to activate the control module 106. Control module 106 controls the equipment 108, using one or more of the control responses listed above. The navigation module 500 in some embodiments includes speech synthesis and/or speech recognition subsystems that can be integrated with little additional cost with the screening module 104 to expand the extent of the screening to include speech communication and speech analysis of the equipment operator 102. The navigation module 500 in one embodiment also provides historical information useful for more accurately screening the equipment operator 102 for impairments.

Figure 6:
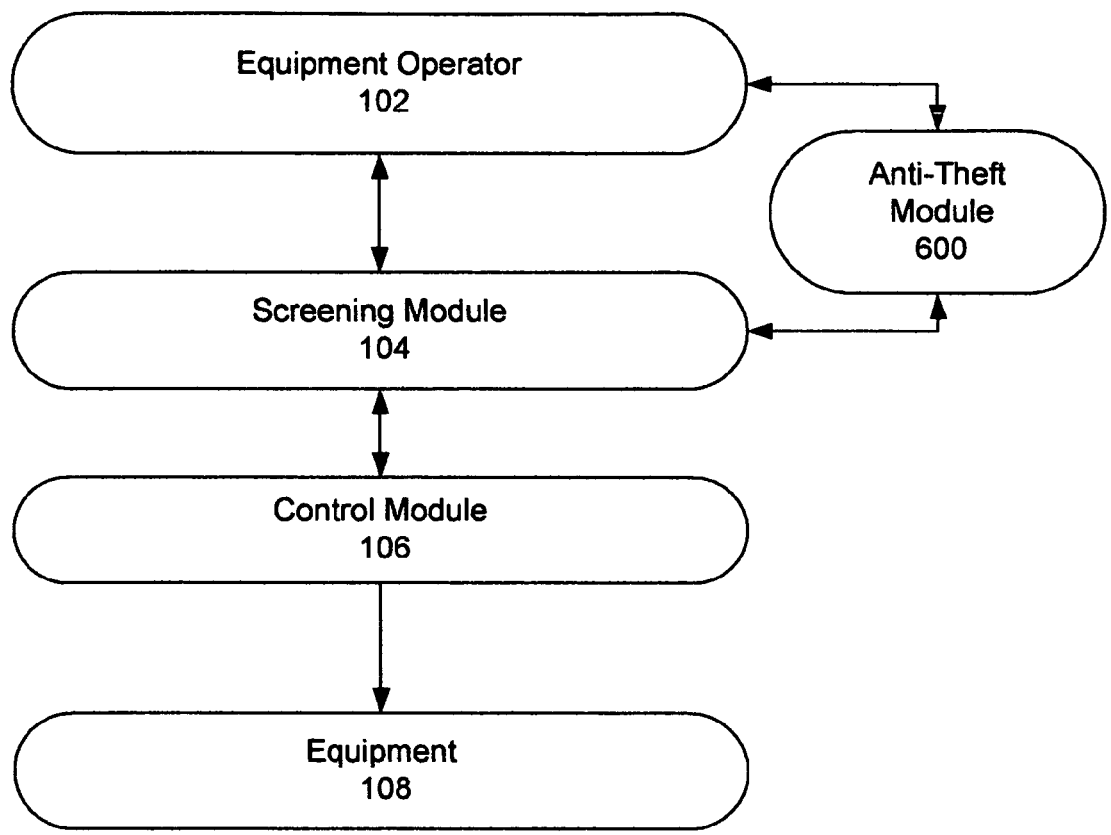
FIG. 6 illustrates a module diagram of a system to screen an equipment operator by utilizing an anti-theft module of the equipment, in accordance with another embodiment of the invention.

FIG. 6 illustrates a module diagram of a system to screen an equipment operator by utilizing an anti-theft module of the equipment, in accordance with another embodiment of the invention shown in FIG. 1. The screening module 104 screens the equipment operator 102 for one or more impairments. The screening module 104 utilizes information from the anti-theft module 600 to determine whether the equipment operator 102 is impaired and whether to activate the control module 106. Control module 106 controls the equipment 108, using one or more of the control responses listed above. The anti-theft module 600 in some embodiments includes speech synthesis and/or speech recognition subsystems that can be integrated with little additional cost with the screening module 104 to expand the extent of the screening to include speech communication and speech analysis of the equipment operator 102. The anti-theft module 600 in one embodiment also provides historical information useful for more accurately screening the equipment operator 102 for impairments.

Figure 7:
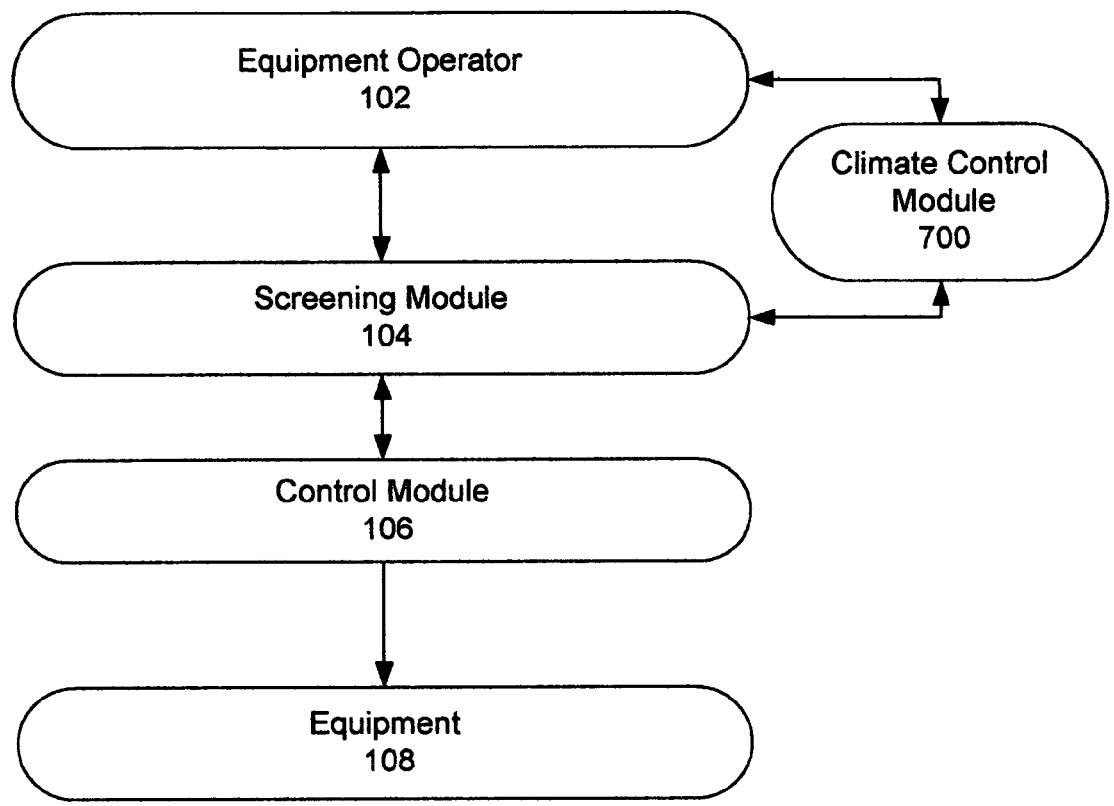
FIG. 7 illustrates a module diagram of a system to screen an equipment operator by utilizing a climate control module of the equipment, in accordance with another embodiment of the invention.

FIG. 7 illustrates a module diagram of a system to screen an equipment operator by utilizing a climate control module of the equipment, in accordance with another embodiment of the invention shown in FIG. 1. The screening module 104 screens the equipment operator 102 for one or more impairments. The screening module 104 utilizes information from the climate control module 700 to determine whether the equipment operator 102 is impaired and whether to activate the control module 106. Control module 106 controls the equipment 108, using one or more of the control responses listed above. The climate control module 700 in some embodiments includes speech synthesis and/or speech recognition subsystems that can be integrated with little additional cost with the screening module 104 to expand the extent of the screening to include speech communication and speech analysis of the equipment operator 102. The climate control module 700 in one embodiment also provides historical information useful for more accurately screening the equipment operator 102 for impairments.

Figure 8:
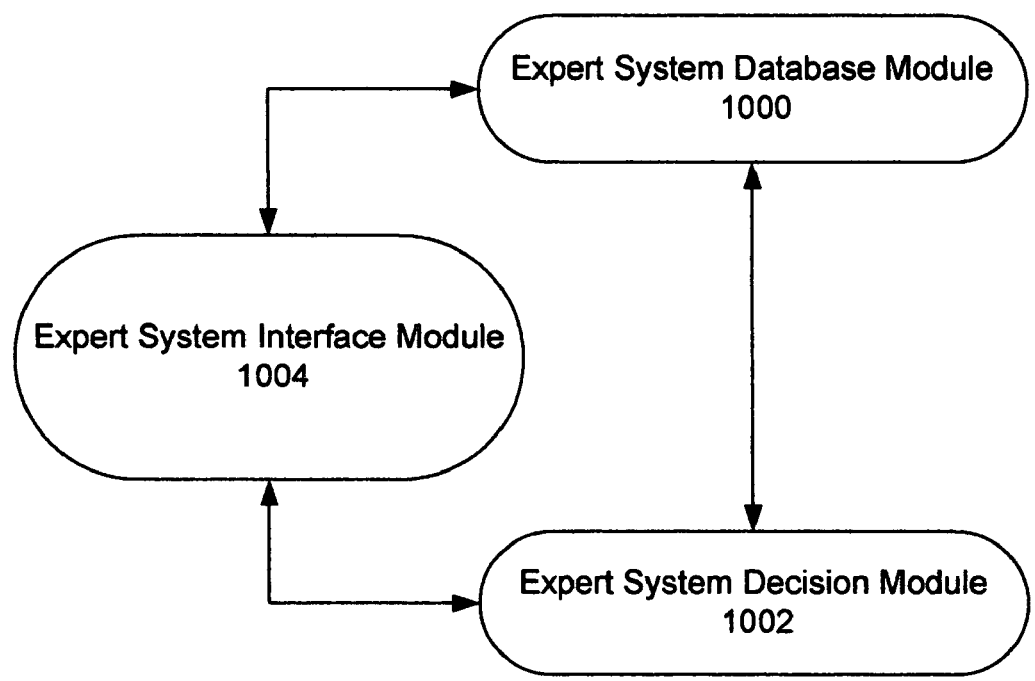
FIG. 8 illustrates an expert system implementation of the screening module shown in FIG. 1 to screen an equipment operator, in accordance with another embodiment of the invention.

FIG. 8 illustrates an expert system implementation of the screening module 104 shown in FIG. 1 to screen an equipment operator, in accordance with another embodiment of the invention. The expert system database module 1000 communicates with the expert system decision module 1002 and the expert system interface module 1004. The expert system database module 1000 stores information useful in determining the impairment of the equipment operator (not shown). The expert system decision module 1002 makes the actual determination of whether or not the equipment operator is impaired and decides which control response to make if there is an impairment. The expert system interface module 1004 obtains information concerning the equipment operator to determine whether or not the equipment operator has a true impairment. The information concerning the equipment operator can be obtained from measuring a characteristic of the equipment operator, such as a chemical in proximity to the equipment operator, electrical resistance of a portion of skin of the equipment operator, breathing rate of the equipment operator, blood pressure of the equipment operator, blood pulse rate of the equipment operator, blood oxygen level of the equipment operator, electrical conductivity of a portion of skin of the equipment operator, temperature of a portion of skin of the equipment operator, one or more optical characteristics of at least one eye of the equipment operator, optical response to at least one stimulus of at least one eye of the equipment operator, at least one speech characteristic of the equipment operator, comparison of at least one speech characteristic of the equipment operator to a sample speech characteristic of the equipment operator, a speed of dexterity of the equipment operator in performing at least one task, a consistency of dexterity of the equipment operator in performing at least one task, asking the equipment operator to perform some task, such as speaking, interpreting a visual pattern, or physically moving some body part (e.g., hands or fingers).

Figure 9:
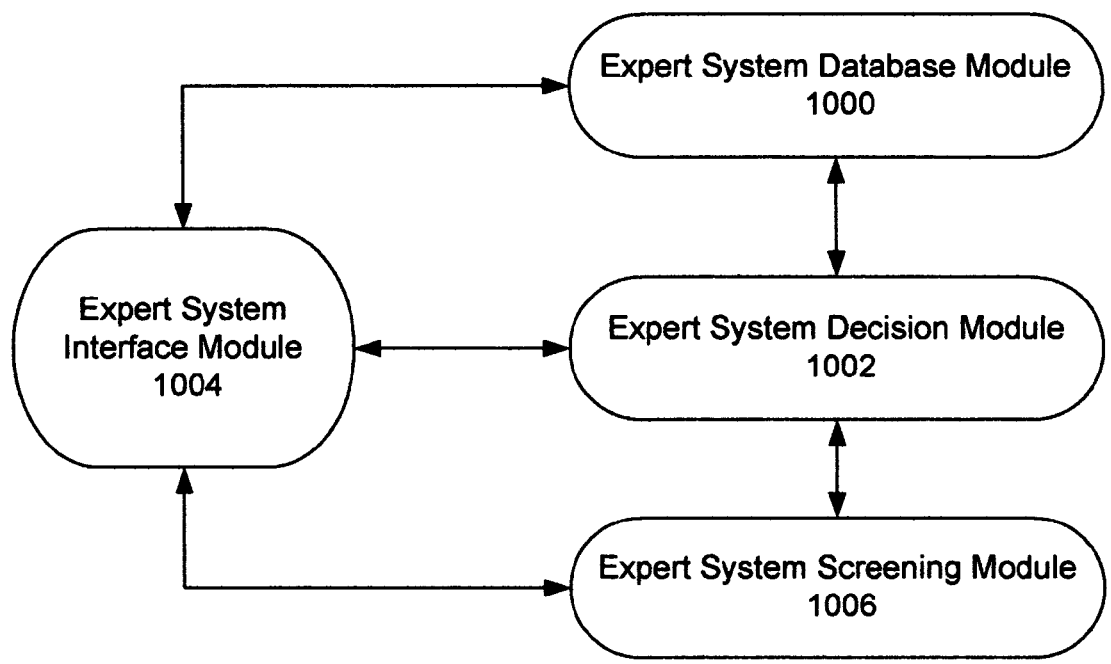
FIG. 9 illustrates an expert system implementation of the screening module shown in FIG. 1 to screen an equipment operator, in accordance with another embodiment of the invention.

FIG. 9 illustrates an expert system implementation of the screening module 104 shown in FIG. 1 to screen an equipment operator, in accordance with another embodiment of the invention. The expert system database module 1000 communicates with the expert system decision module 1002 and the expert systems interface module 1004. The expert system screening module 1006 communicates with the expert system decision module 1002 and the expert system interface module 1004. The expert system database module 1000 stores information useful in determining the impairment of the equipment operator (not shown). The expert system decision module 1002 makes the actual determination of whether or not the equipment operator is impaired and decides which control response to make if there is an impairment. The expert system screening module 1006 assists in screening and selectively testing the equipment operator, and assists the expert system decision module 1002 in determining whether the equipment operator has a true impairment. The expert system interface module 1004 is used to obtain information concerning the equipment operator to determine whether or not the equipment operator has a true impairment. The expert system other factors module 1008 communicates with the expert system screening module 1006 and the expert system interface module 1004, and provides additional information that is used to adapt and/or interpret the screening of the equipment operator to more accurately determine whether the equipment operator has a true impairment.

Figure 10:
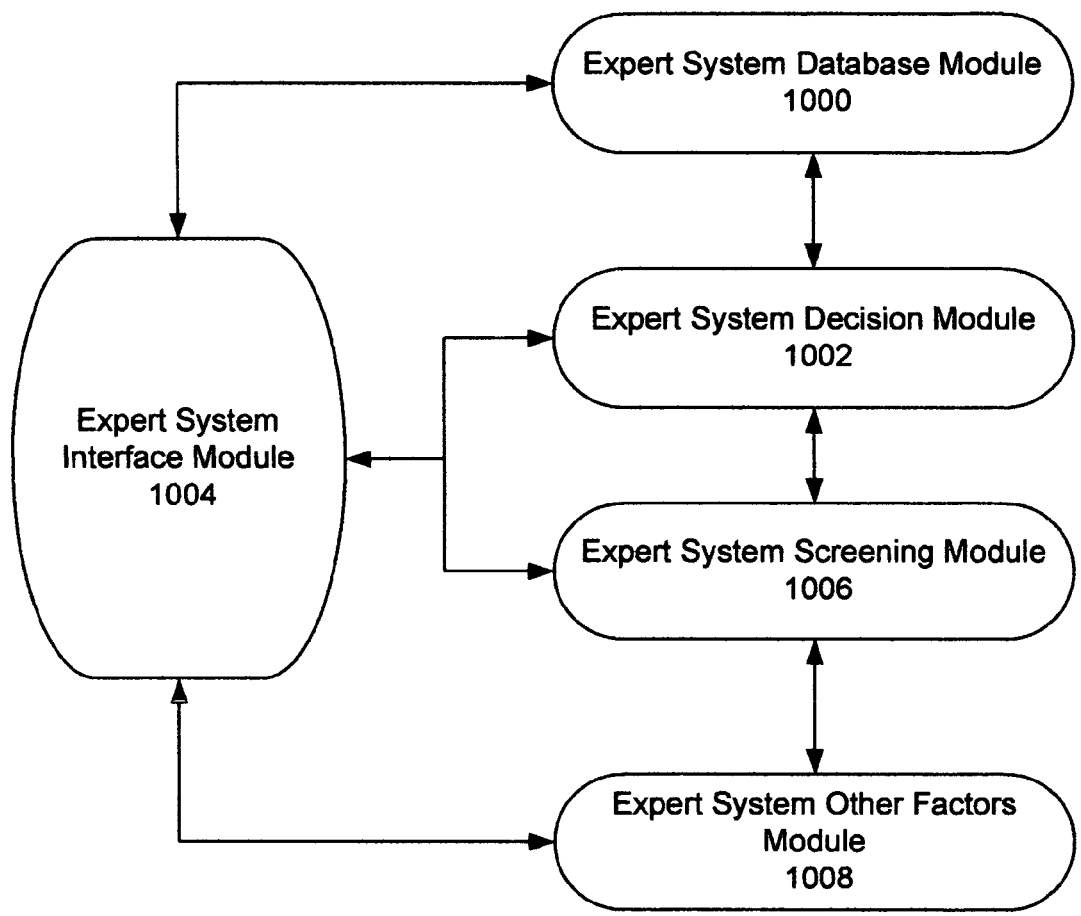
FIG. 10 illustrates an expert system implementation of the screening module shown in FIG. 1 to screen an equipment operator, in accordance with another embodiment of the invention.

FIG. 10 illustrates an expert system implementation of the screening module 104 shown in FIG. 1 to screen an equipment operator, in accordance with another embodiment of the invention. The expert system database module 1000 communicates with the expert system decision module 1002 and the expert system interface module 1004. In this embodiment, the expert system interface module 1004 resides within one or more existing equipment module(s) previously listed (e.g., an operations module, an audio module, a navigation module, an anti-theft module, a climate control module, or an equivalent module normally associated with the equipment).

Figure 11:
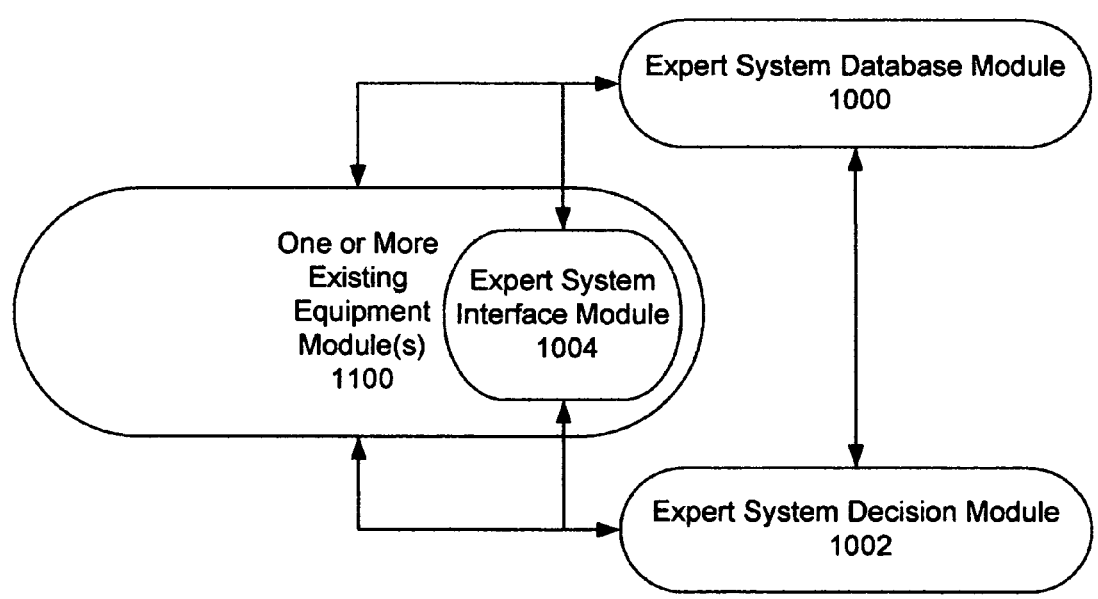
FIG. 11 illustrates an expert system implementation of the screening module shown in FIG. 1 to screen an equipment operator, in accordance with another embodiment of the invention.

FIG. 11 illustrates an expert system implementation of the screening module 104 shown in FIG. 1 to screen an equipment operator, in accordance with another embodiment of the invention. The expert system database module 1000 communicates with the expert system decision module 1002 and the expert system interface module 1004. In this embodiment, the expert system interface module 1004 resides within one or more existing equipment module(s) previously listed (e.g., an operations module, an audio module, a navigation module, an anti-theft module, a climate control module, or an equivalent module normally associated with the equipment). For example, in one embodiment the expert system interface module 1004 resides within an operations module of the equipment. In another embodiment the expert system interface module 1004 resides within an audio module of the equipment. In another embodiment the expert system interface module 1004 resides within a navigation module of the equipment.

Figure 12:
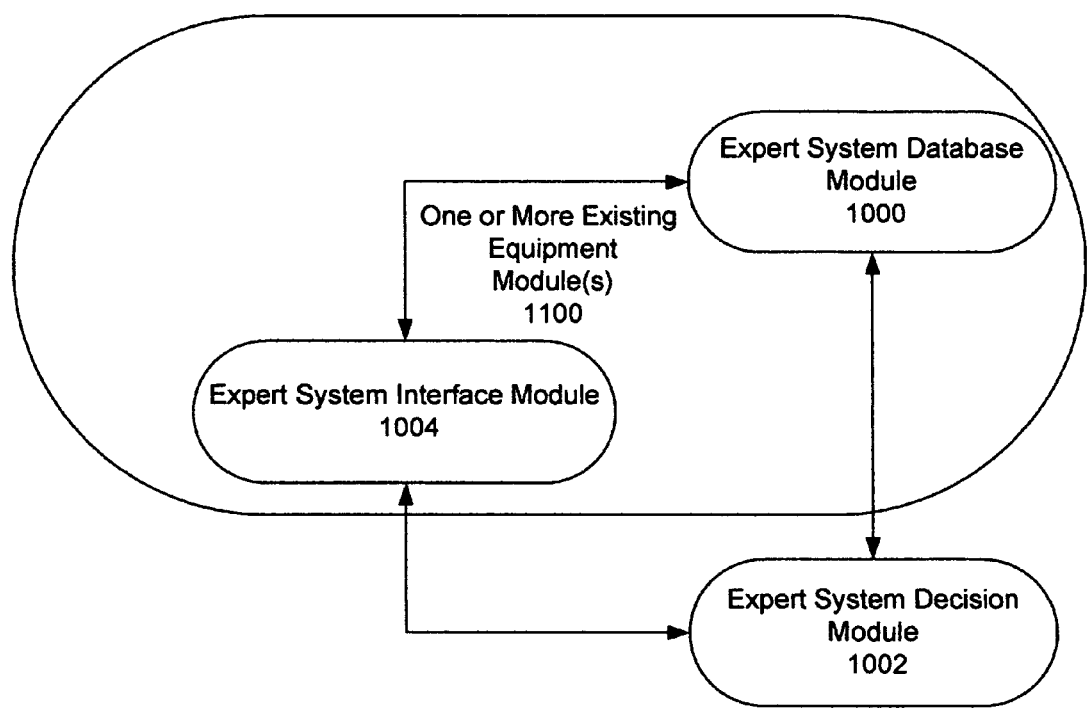
FIG. 12 illustrates an expert system implementation of the screening module shown in FIG. 1 to screen an equipment operator, in accordance with another embodiment of the invention.

FIG. 12 illustrates an expert system implementation of the screening module 104 shown in FIG. 1 to screen an equipment operator, in accordance with another embodiment of the invention. The expert system database module 1000 communicates with the expert system decision module 1002 and the expert system interface module 1004. In this embodiment, the expert system database module 1000 and the expert system interface module 1004 reside within one or more existing equipment module(s) previously listed (e.g., an operations module, an audio module, a navigation module, an anti-theft module, a climate control module, or an equivalent module normally associated with the equipment). For example, in one embodiment the expert system database module 1000 and the expert system interface module 1004 reside within the same operations module of the equipment. In another embodiment the expert system database module 1000 resides in an operations module, and the expert system interface module 1004 resides within an audio module. In another embodiment the expert system database module 1000 resides in a navigation module, and the expert system interface module 1004 resides within an operations module.

Figure 13:
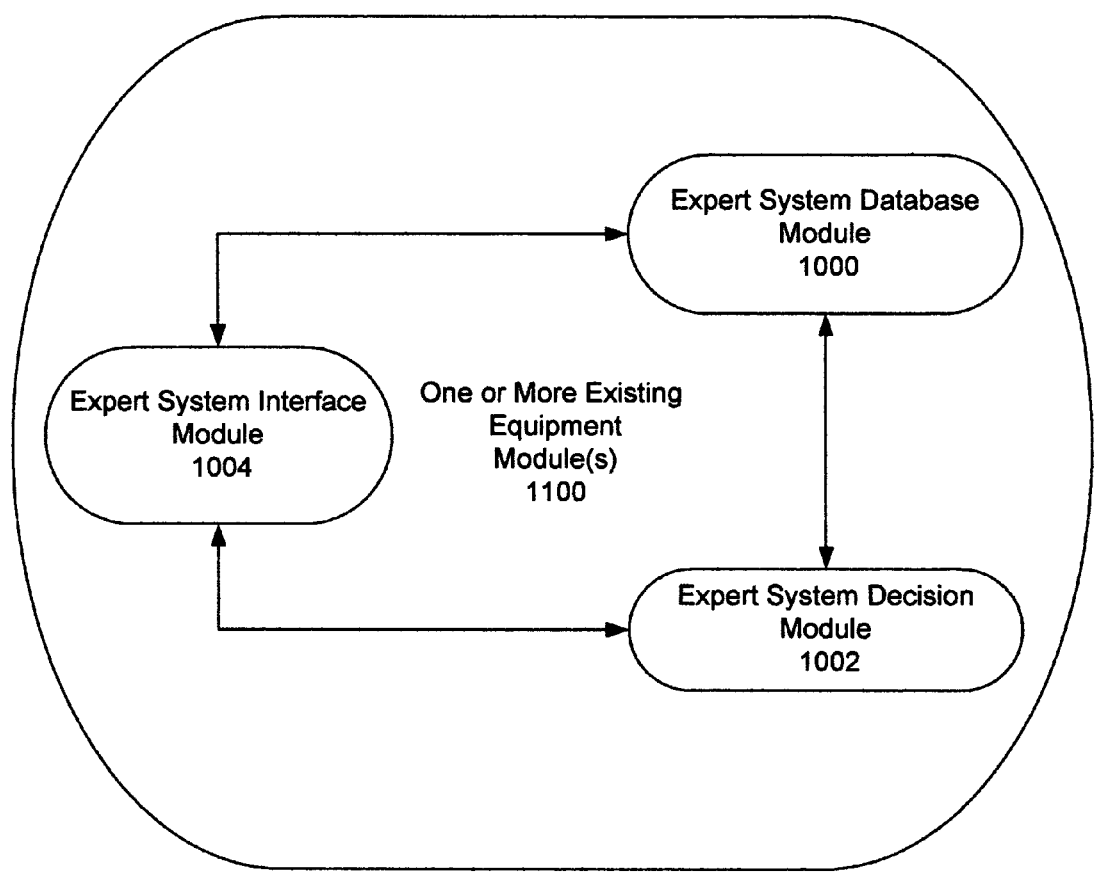
FIG. 13 illustrates an expert system implementation of the screening module shown in FIG. 1 to screen an equipment operator, in accordance with another embodiment of the invention.

FIG. 13 illustrates an expert system implementation of the screening module 104 shown in FIG. 1 to screen an equipment operator, in accordance with another embodiment of the invention. The expert system database module 1000 communicates with the expert system decision module 1002 and the expert system interface module 1004. In this embodiment, the expert system database module 1000, the expert system decision module 1002, and the expert system interface module 1004 reside within one or more existing equipment module(s) previously listed (e.g., an operations module, an audio module, a navigation module, an anti-theft module, a climate control module, or an equivalent module normally associated with the equipment). For example, in one embodiment the expert system database module 1000, the expert system decision module 1002, and the expert system interface module 1004 all reside within the same existing equipment module chosen from the previous list. In another embodiment the three expert system modules are spread among multiple existing equipment modules. Less cabling and a faster response time are two advantages in locating the expert system database module 1000, the expert system decision module 1002, and the expert system interface module 1004 within the same existing equipment module. However, there may not be enough available processor time and memory in one existing equipment module to support the entire expert system. Furthermore, in one embodiment, the screening module 104 shown in FIG. 1 is actually composed of one or more expert systems for determining different types of equipment operator impairments, and portions of each expert system can be consolidated or distributed among one or more existing equipment module(s) previously listed.

Figure 14:
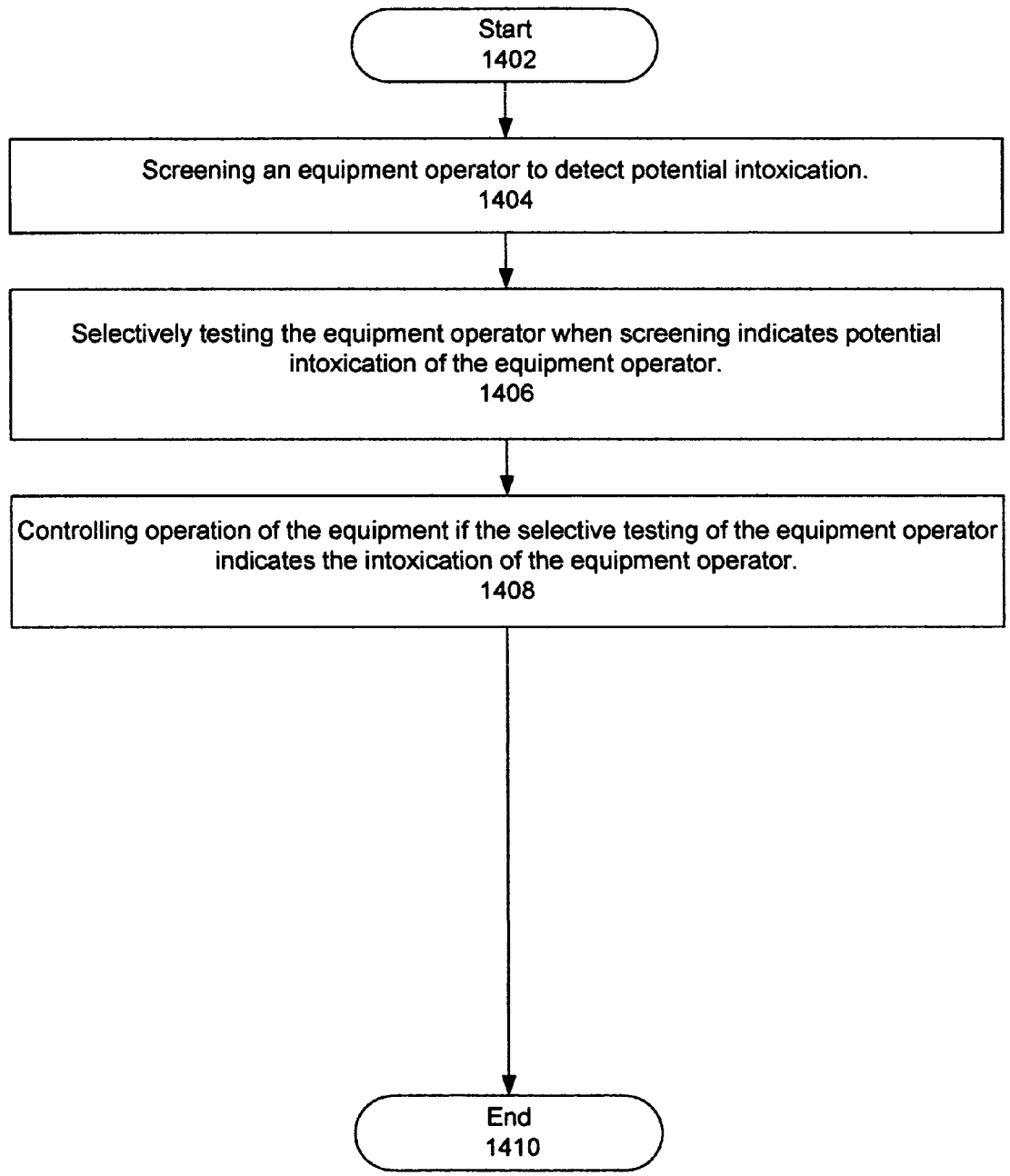
FIG. 14 illustrates a flowchart to screen an equipment operator, in accordance with another embodiment of the invention.

FIG. 14 illustrates a flowchart to screen an equipment operator, in accordance with another embodiment of the invention. The method starts in operation 1402. Operation 1404 is next and includes screening an equipment operator to detect potential intoxication. Operation 1406 is next and includes selectively testing the equipment operator when the screening indicates potential intoxication of the equipment operator. Operation 1408 is next and includes controlling the operation of the equipment if the selective testing of the equipment operator indicates the intoxication of the equipment operator. Controlling the operation of the equipment can include one or more of the following control responses: disabling the equipment, disabling the equipment after a time delay, temporarily disabling the equipment for a pre-selected time duration, shutting off power to the equipment, limiting the operation of the equipment to a lower speed of operation, limiting the operation of the equipment to allow only the return the equipment to a pre-selected state or a pre-selected location, sending a warning message to another entity for assistance, issuing a warning message to the operator, and/or requesting another equipment operator replace the impaired equipment operator and then disabling the equipment if the request is not obeyed within a short time. The method ends in operation 1410.

Figure 15:
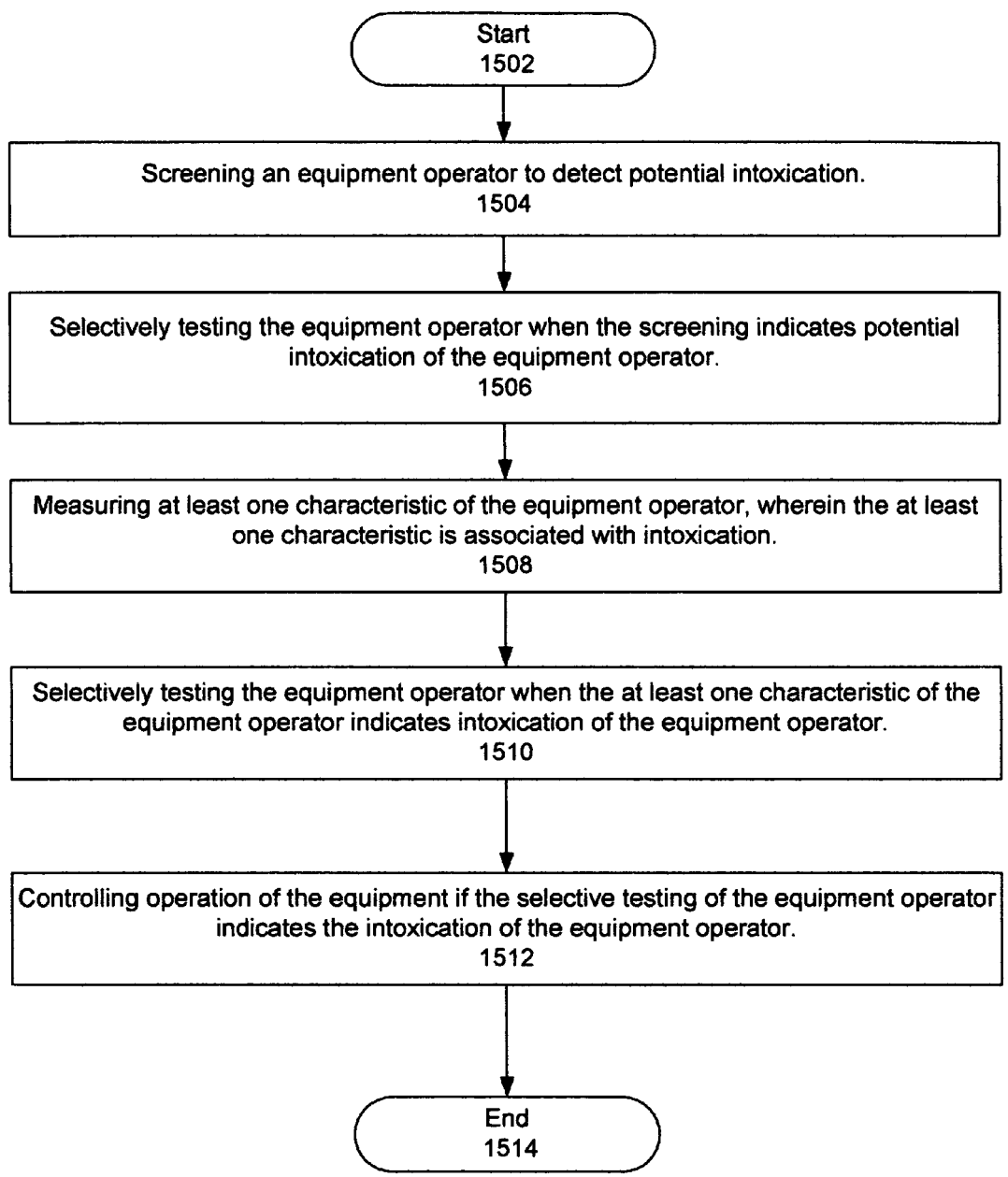
FIG. 15 illustrates a flowchart to screen an equipment operator, in accordance with another embodiment of the invention.

FIG. 15 illustrates a flowchart to screen an equipment operator, in accordance with one embodiment of the invention. The method starts in operation 1502. Operation 1504 is next and includes screening an equipment operator to detect potential intoxication. Operation 1506 is next and includes selectively testing the equipment operator when the screening indicates potential intoxication of the equipment operator. Operation 1508 is next and includes measuring at least one characteristic of the equipment operator, wherein the at least one characteristic is associated with intoxication. Operation 1510 is next and includes selectively testing the equipment operator when at least one characteristic of the equipment operator indicates the intoxication of the equipment operator. Operation 1512 is next and includes controlling the operation of the equipment if the selective testing of the equipment operator indicates the intoxication of the equipment operator. The controlling operation can include one or more of the control responses listed above. The method ends in operation 1514.

Figure 16:
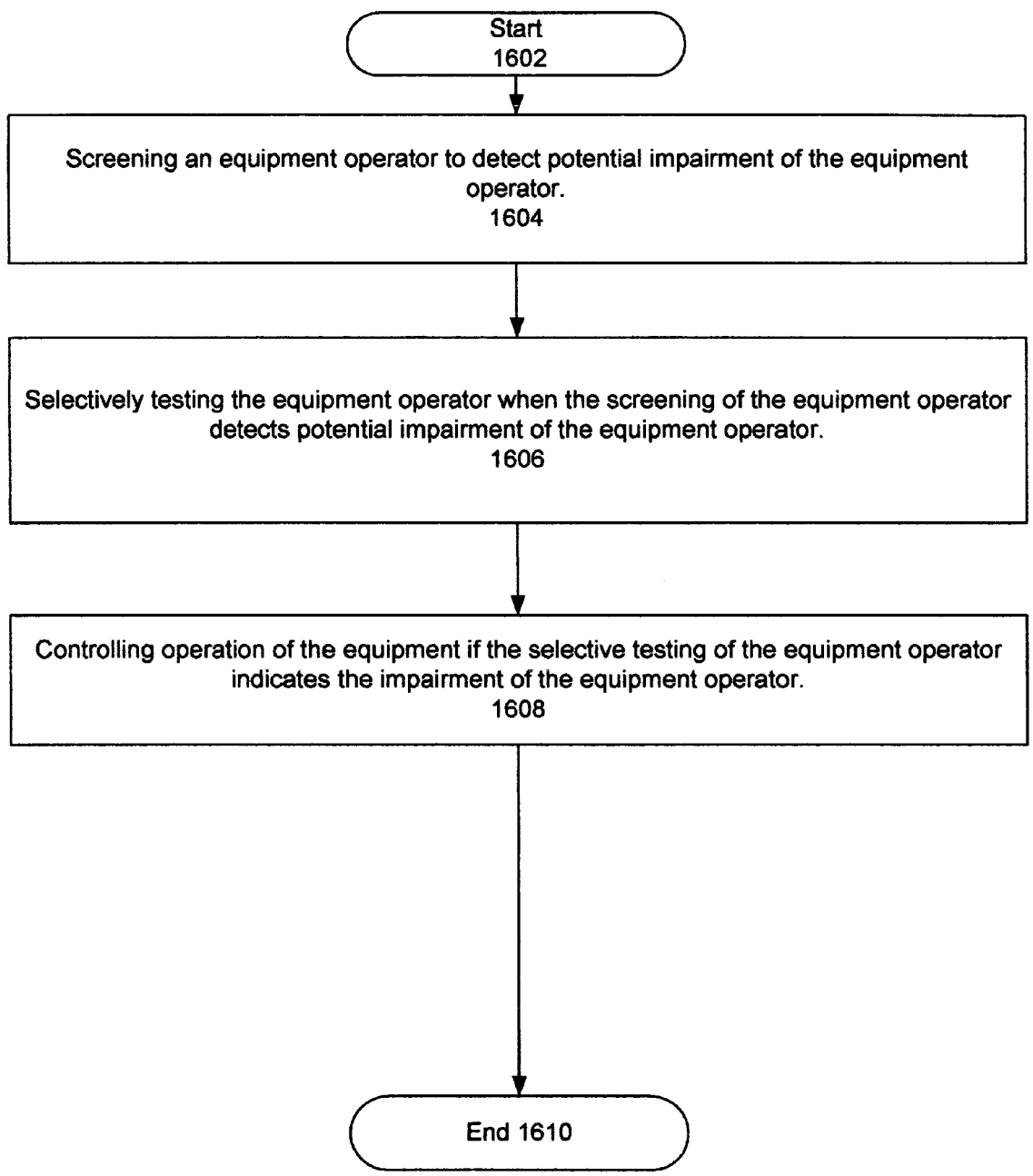
FIG. 16 illustrates another flowchart to screen an equipment operator, in accordance with another embodiment of the invention.

FIG. 16 illustrates another flowchart to screen an equipment operator, in accordance with one embodiment of the invention. The method starts in operation 1602. Operation 1604 is next and includes screening an equipment operator to detect potential impairment of an equipment operator. Operation 1606 is next and includes selectively testing the equipment operator when the screening of the equipment operator detects potential impairment of the equipment operator. Operation 1608 is next and includes controlling the operation of the equipment if the selective testing of the equipment operator indicates the impairment of the equipment operator. The controlling operation can include one or more of the control responses listed above. The method ends in operation 1610.

Other embodiments of the invention are possible. For example, other factors could be considered in screening the equipment operator, such as shaking of the equipment, sudden starts and stops of the equipment, or wild fluctuations in the operation of one or more modules listed above (e.g., operations module, audio module, navigation module, anti-theft module, or the climate control module). Another embodiment can deny operator entry through the doors of enclosed equipment (e.g., autos, campers, recreational vehicles, trains, ships, airplanes, and so forth).

The exemplary embodiments described herein are for purposes of illustration and are not intended to be limiting. For example, when elements of "one embodiment" are disclosed, this does not imply that the elements must be incorporated in "all embodiments." Therefore, those skilled in the art will recognize that other embodiments could be practiced without departing from the scope and spirit of the claims set forth below.

What is claimed is:

1. A method to screen an equipment operator for intoxication, comprising:
   screening an equipment operator by one or more expert systems to measure at least one type of chemical in the air in proximity to the equipment operator to detect potential intoxication;
   selectively testing said equipment operator when said screening indicates potential intoxication of said equipment operator; and
   controlling operation of said equipment if said selective testing of said equipment operator indicates said intoxication of said equipment operator.

2. The method of claim 1, wherein said screening of said equipment operator includes utilization of information derived from one or more existing equipment modules selected from the group of existing equipment modules consisting of: an operations module, an audio module, a navigation module, an anti-theft module, and a climate control module.

3. The method of claim 1, further comprising:
   allowing one or more people in proximity to said equipment operator to activate a screening of said equipment operator for intoxication by one or more expert systems.

4. The method of claim 1, further comprising measuring at least one characteristic of said equipment operator including one or more characteristics selected from the group consisting of: at least one chemical in proximity to said equipment operator, breathing rate of said equipment operator, blood pressure of said equipment operator, blood pulse rate of said equipment operator, blood oxygen level of said equipment operator, electrical resistance of a portion of skin of said equipment operator, electrical conductivity of a portion of skin of said equipment operator, temperature of a portion of skin of said equipment operator, one or more optical characteristics of at least one eye of said equipment operator, optical response to at least one stimulus of at least one eye of the equipment operator, at least one speech characteristic of said equipment operator, comparison of at least one speech characteristic of said equipment operator to a reference speech characteristic of said equipment operator, a speed of dexterity of said equipment operator in performing at least one task, and a consistency of dexterity of said equipment operator in performing at least one task.

5. The method of claim 1, wherein said selective testing of said equipment operator includes utilization of information derived from one or more existing equipment modules selected from the group of existing equipment modules consisting of: an operations module, an audio module, a navigation module, an anti-theft module, and a climate control module.

6. The method of claim 1, wherein said controlling operation of said equipment includes one or more control responses selected from the group of control responses consisting of: disabling said equipment, disabling said equipment after a time delay, temporarily disabling said equipment for a pre-selected time duration, shutting off power to said equipment, limiting operation of said equipment to a lower speed of operation, limiting the operation of said equipment to allow only return of said equipment to a pre-selected state, limiting the operation of said equipment to allow return of said equipment to a pre-selected location, autonomously moving said equipment to another location, denying entry to said equipment, activating an alarm, sending a warning message to another entity for assistance, issuing a warning message to an impaired equipment operator, and making a request for another equipment operator to replace an impaired equipment operator and then restricting operation of said equipment if said request is not obeyed within a pre-selected time.

7. The method of claim 1, wherein said selective testing utilizes one or more other factors chosen from the group of factors consisting of air temperature, oxygen level, carbon dioxide level, carbon monoxide levels, nitrous oxide levels, hydrocarbon vapor levels, the presence of any gas associated with impairment, air humidity, air pressure, time of day, time duration of vehicle parking, voice loudness levels in proximity to said equipment, history of operation of said equipment by said equipment operator, initial beginning of operation of said equipment by said equipment operator, and ongoing operation of said equipment by said equipment operator.

8. A method to screen an equipment operator for impairment, comprising:
    screening an equipment operator by one or more expert systems to detect potential impairment of said equipment operator;
    selectively testing said equipment operator when said screening of said equipment operator detects potential impairment of said equipment operator; and
    controlling operation of said equipment if said selective testing of said equipment operator indicates said impairment of said equipment operator, wherein said screening of said equipment operator includes a time-sharing allocation of at least one processor executing at least one expert system.

9. The method of claim 8, wherein said screening of said equipment operator includes utilization of at least a portion of one or more existing equipment modules selected from the group of existing equipment modules consisting of: an operations module, an audio module, a navigation module, an anti-theft module, and a climate control module.

10. The method of claim 8, further comprising:
    allowing one or more people in proximity to said equipment operator to activate a screening of said equipment operator for impairment by one or more expert systems.

11. The method of claim 8, further comprising measuring at least one characteristic of said equipment operator including one or more characteristics selected from the group consisting of: at least one chemical in proximity to said equipment operator, breathing rate of said equipment operator, blood pressure of said equipment operator, blood pulse rate of said equipment operator, blood oxygen level of said equipment operator, electrical resistance of a portion of skin of said equipment operator, electrical conductivity of a portion of skin of said equipment operator, temperature of a portion of skin of said equipment operator, one or more optical characteristics of at least one eye of said equipment operator, optical response to at least one stimulus of at least one eye of said equipment operator, at least one speech characteristic of said equipment operator, comparison of at least one speech characteristic of said equipment operator to a reference speech characteristic of said equipment operator, a speed of dexterity of said equipment operator in performing at least one task, and a consistency of dexterity of said equipment operator in performing at least one task.

12. The method of claim 8, wherein said selective testing of said equipment operator includes utilization of at least a portion of one or more existing equipment modules selected from the group of existing equipment modules consisting of: an operations module, an audio module, a navigation module, an anti-theft module, and a climate control module.

13. The method of claim 8, wherein said controlling operation of said equipment includes one or more control responses selected from the group of control responses consisting of: disabling said equipment, disabling said equipment after a time delay, temporarily disabling said equipment for a pre-selected time duration, shutting off power to said equipment, limiting operation of said equipment to a lower speed of operation, limiting the operation of said equipment to allow only return of said equipment to a pre-selected state, limiting the operation of said equipment to allow return of said equipment to a pre-selected location, autonomously moving said equipment to another location, denying entry to said equipment, activating an alarm, sending a warning message to another entity for assistance, issuing a warning message to an impaired equipment operator, and making a request for another equipment operator to replace an impaired equipment operator and then restricting operation of said equipment if said request is not obeyed within a pre-selected time.

14. The method of claim 8, wherein said selective testing of said equipment operator includes a time-sharing allocation of one or more processors of one or more existing equipment modules executing one or more expert systems.

15. The method of claim 8, wherein said selective testing selectively changes according to one or more other factors chosen from the group of factors consisting of air temperature, oxygen level, carbon dioxide level, carbon monoxide levels, nitrous oxide levels, hydrocarbon vapor levels, the presence of any gas associated with impairment, air humidity, air pressure, time of day, time duration of vehicle parking, voice loudness levels in proximity to said equipment, history of operation of said equipment by said equipment operator, initial beginning of operation of said equipment by said equipment operator, and ongoing operation of said equipment by said equipment operator.

16. A system to screen an equipment operator, comprising:
    a screening module to screen and selectively test an equipment operator when said screening indicates potential impairment of said equipment operator, wherein said screening module utilizes one or more expert system modules in screening said equipment operator; and
    a control module to control operation of said equipment if said selective testing of said equipment operator indicates said impairment of said equipment operator, wherein said screening module includes one or more expert system modules that utilize at least a portion of one or more equipment modules selected from the group of equipment modules consisting of: an operations module, an audio module, a navigation module, an anti-theft module, and a climate control module.

17. The system of claim 16, wherein said control module to control operation of said equipment uses one or more control responses selected from the group of control responses consisting of: disabling said equipment, disabling said equipment after a time delay, temporarily disabling said equipment for a pre-selected time duration, shutting off power to said equipment, limiting operation of said equipment to a lower speed of operation, limiting the operation of said equipment to allow only return of said equipment to a pre-selected state, limiting the operation of said equipment to allow return of said equipment to a pre-selected location autonomously moving said equipment to another location, denying entry to said equipment, activating an alarm, sending a warning message to another entity for assistance, issuing a warning message to an impaired equipment operator, and requesting replacement of a first equipment operator by a second equipment operator and restricting operation of said equipment if said request is not obeyed within a pre-selected time.

18. The system of claim 16, wherein said screening module includes at least one module to measure at least one characteristic of said equipment operator selected from the group of characteristics consisting of: at least one chemical in proximity to said equipment operator, electrical resistance of a portion of skin of said equipment operator, breathing rate of said equipment operator, blood pressure of said equipment operator, blood pulse rate of said equipment operator, blood oxygen level of said equipment operator, electrical conductivity of a portion of skin of said equipment operator, temperature of a portion of skin of said equipment operator, one or more optical characteristics of at least one eye of said equipment operator, optical response to at least one stimulus of at least one eye of said equipment operator, at least one speech characteristic of said equipment operator, comparison of at least one speech characteristic of said equipment operator to a reference speech characteristic of said equipment operator, a speed of dexterity of said equipment operator in performing at least one task, and a consistency of dexterity of said equipment operator in performing at least one task.

* * * * *